United States Patent
Link et al.

(10) Patent No.: US 7,175,662 B2
(45) Date of Patent: Feb. 13, 2007

(54) CERVICAL INTERVERTEBRAL PROSTHESIS

(75) Inventors: Helmut D. Link, Hamburg (DE); Paul C. McAfee, Baltimore, MD (US)

(73) Assignee: Cervitech, Inc., Rockaway, NJ (US)

( * ) Notice: Subject to any disclaimer, the term of this patent is extended or adjusted under 35 U.S.C. 154(b) by 0 days.

(21) Appl. No.: 10/814,783

(22) Filed: Apr. 1, 2004

(65) Prior Publication Data

US 2005/0222682 A1   Oct. 6, 2005

(51) Int. Cl.
  *A61F 2/44* (2006.01)
(52) U.S. Cl. .................................. 623/17.11
(58) Field of Classification Search .. 623/17.11–17.16; 606/61, 69–71, 99, 105
  See application file for complete search history.

(56) References Cited

U.S. PATENT DOCUMENTS

| | | | | |
|---|---|---|---|---|
| 2,181,746 A | * | 11/1939 | Siebrandt | 606/96 |
| 2,507,710 A | * | 5/1950 | Grosso | 606/205 |
| 4,401,112 A | * | 8/1983 | Rezaian | 606/61 |
| 4,444,180 A | * | 4/1984 | Schneider et al. | 606/96 |
| 4,502,475 A | * | 3/1985 | Weigle et al. | 606/105 |
| 5,236,460 A | * | 8/1993 | Barber | 623/17.15 |
| 5,246,458 A | * | 9/1993 | Graham | 623/17.14 |
| 5,258,031 A | * | 11/1993 | Salib et al. | 623/17.15 |
| 5,370,697 A | * | 12/1994 | Baumgartner | 623/17.15 |
| 5,380,324 A | * | 1/1995 | Muller et al. | 606/61 |
| 5,395,372 A | * | 3/1995 | Holt et al. | 606/61 |
| 5,425,773 A | * | 6/1995 | Boyd et al. | 623/17.15 |
| 5,442,515 A | * | 8/1995 | Wallaert | 361/187 |
| 5,458,641 A | * | 10/1995 | Ramirez Jimenez | 623/17.11 |
| 5,674,296 A | * | 10/1997 | Bryan et al. | 623/17.16 |
| 5,676,666 A | * | 10/1997 | Oxland et al. | 606/61 |
| 5,697,933 A | * | 12/1997 | Gundlapalli et al. | 606/96 |
| 5,702,455 A | * | 12/1997 | Saggar | 623/17.15 |
| 5,895,428 A | * | 4/1999 | Berry | 623/17.15 |
| 6,120,503 A | * | 9/2000 | Michelson | 606/61 |
| 6,228,085 B1 | * | 5/2001 | Theken et al. | 606/61 |
| 6,342,057 B1 | * | 1/2002 | Brace et al. | 606/96 |
| 6,379,364 B1 | * | 4/2002 | Brace et al. | 606/96 |
| 6,436,103 B1 | * | 8/2002 | Suddaby | 606/96 |
| 6,461,359 B1 | * | 10/2002 | Tribus et al. | 606/61 |
| 6,682,562 B2 | * | 1/2004 | Viart et al. | 623/17.14 |
| 6,692,503 B2 | * | 2/2004 | Foley et al. | 606/96 |
| 2001/0047172 A1 | * | 11/2001 | Foley et al. | 606/69 |
| 2002/0082606 A1 | * | 6/2002 | Suddaby | 606/96 |
| 2003/0120274 A1 | * | 6/2003 | Morris et al. | 606/61 |
| 2003/0204260 A1 | * | 10/2003 | Ferree | 623/17.11 |
| 2005/0165486 A1 | * | 7/2005 | Trieu | 623/17.13 |

(Continued)

FOREIGN PATENT DOCUMENTS

FR    2822674 A    10/2002

(Continued)

*Primary Examiner*—Eduardo C. Robert
*Assistant Examiner*—Annette Reimers
(74) *Attorney, Agent, or Firm*—Morrison & Foerster LLP

(57) ABSTRACT

A cervical intervertebral prosthesis includes at least one cover plate that is configured to be connected to one of its two adjacent vertebral bodies and a securing plate which secures this cover plate and is configured to be fastened to the ventral surface of the vertebral body. The securing plate may be a separate part that is unconnected to the cover plate and can be biodegradable.

4 Claims, 1 Drawing Sheet

U.S. PATENT DOCUMENTS

2005/0187631 A1* 8/2005 Van Hoeck et al. ..... 623/17.13

FOREIGN PATENT DOCUMENTS

| WO | WO-00/66011 A | | 11/2000 | |
| WO | WO-02/09626 A | | 2/2002 | |
| WO | WO 02/45592 | * | 6/2002 | ............ 606/61 |
| WO | WO-02/45592 A | | 6/2002 | |
| WO | WO-03/075804 A | | 9/2003 | |

* cited by examiner

CERVICAL INTERVERTEBRAL PROSTHESIS

FIELD AND BACKGROUND OF THE INVENTION

Cervical intervertebral prostheses are known (EP-A-1 344 508) having two cover plates which are to be connected to the end plates of the adjacent vertebral bodies and between which there is a sliding core which allows the cover plates a relative movement intended to simulate the articulated mobility of the intervertebral disk that has been replaced. To secure the cover plates in their intended position between the vertebral bodies, the cover plates in the known prosthesis are connected to securing plates which extend from the ventral edge of the cover plates, perpendicularly thereto, and are screwed to the ventral surface of the associated vertebral body. The ventral surfaces of the vertebral bodies on which the securing plates come to lie do not always extend exactly perpendicular with respect to the end plates of the vertebral bodies on which the main surfaces of the cover plates come to lie. This prevents the securing plates from bearing across their entire surface on the vertebral bodies, and it impairs the stability of the cover plates.

SUMMARY OF THE INVENTION

This shortcoming is remedied by the features of the invention as forth in this application. According to this, the securing plate is a separate part which is unconnected to the cover plate. Consequently, the securing plate, independently of the position of the cover plate, can assume the attitude corresponding to the position and shape of the ventral surface of the vertebral body. In this way, an optimal fastening of the securing plate on the vertebral body is possible. It protrudes with a limit stop part in front of the intervertebral space and thereby ensures that the associated cover plate cannot escape in the ventral direction. Therefore, the securing function of the securing plate is not impaired by the fact that it is separate from the cover plate. However, it is unable to prevent the cover plate from shifting in the dorsal direction. The invention is therefore preferably intended for those cover plates which are equipped with suitable means for preventing this dorsal movement. Cover plates provided with a dorsally facing limit stop surface (WO-A-03 075 804) are therefore especially suitable.

However, it is unable to prevent the cover plate from shifting in the dorsal direction. The invention is therefore preferably intended for those cover plates which are equipped with suitable means for preventing this dorsal movement. Cover plates provided with a dorsally facing limit stop surface (WO-A-03 075 804) are therefore especially suitable.

An important advantage of the invention is that it allows the cover plate to be used with or without securing plate. For this, it was hitherto necessary to keep different cover plates in stock, namely those with and those without securing plate.

A further advantage of the invention is that micro movements of the cover plate, which may occur as a result of normal neck movement, are not transmitted to the securing plate and, therefore, cannot lead to loosening of its fastening means. Nevertheless, it may be expedient to equip the fastening screws with a device securing them against inadvertent loosening.

In connection with one prosthesis, it is possible to use two securing plates which are fastened, lying opposite one another, on the adjacent vertebral bodies, in order to secure one or other cover plate of the prosthesis. In general, however, it suffices to secure one cover plate with a securing plate in order to effectively prevent all parts of the prosthesis from escaping in the ventral direction from the intervertebral space.

It will be appreciated that the securing plate should have a predetermined position in relation to the cover plate. It should in fact extend sufficiently over the vertebral body and in front of the intervertebral space in order to be able to accomplish the securing function. On the other hand, it should not protrude too far, so as not to impede the relative movement of the vertebral bodies or of the prosthesis parts with respect to one another during the articulation movement. In order to position the securing plate, it is therefore expedient to use an instrument designed as a drill gauge for the fastening screws of the securing plate. This drill gauge can be provided with means giving it a predetermined position in relation to the implanted prosthesis. Instead of this, it can also interact with, or be fixedly connected to, a prosthesis model which is fitted into the intervertebral space prior to implantation of the prosthesis.

According to a special feature of the invention, the securing plate can be biodegradable. For this purpose, the material is chosen and dimensioned in such a way that it remains in situ and can perform its securing function at least for the period of time until the associated cover plate of the prosthesis has connected definitively to the adjoining bone tissue. As soon as this is the case, i.e. when the bone tissue has connected to the surface of the cover plate so intimately that a relative displacement is no longer possible under the forces that apply, the securing plate is no longer necessary. The time required for this to happen is of the order of several months, for example two to six months.

BRIEF DESCRIPTION OF THE DRAWINGS

The invention is explained in more detail below with reference to the drawings which depict an advantageous illustrative embodiment, and in which.

DETAILED DESCRIPTION OF THE INVENTION

Figure 1:
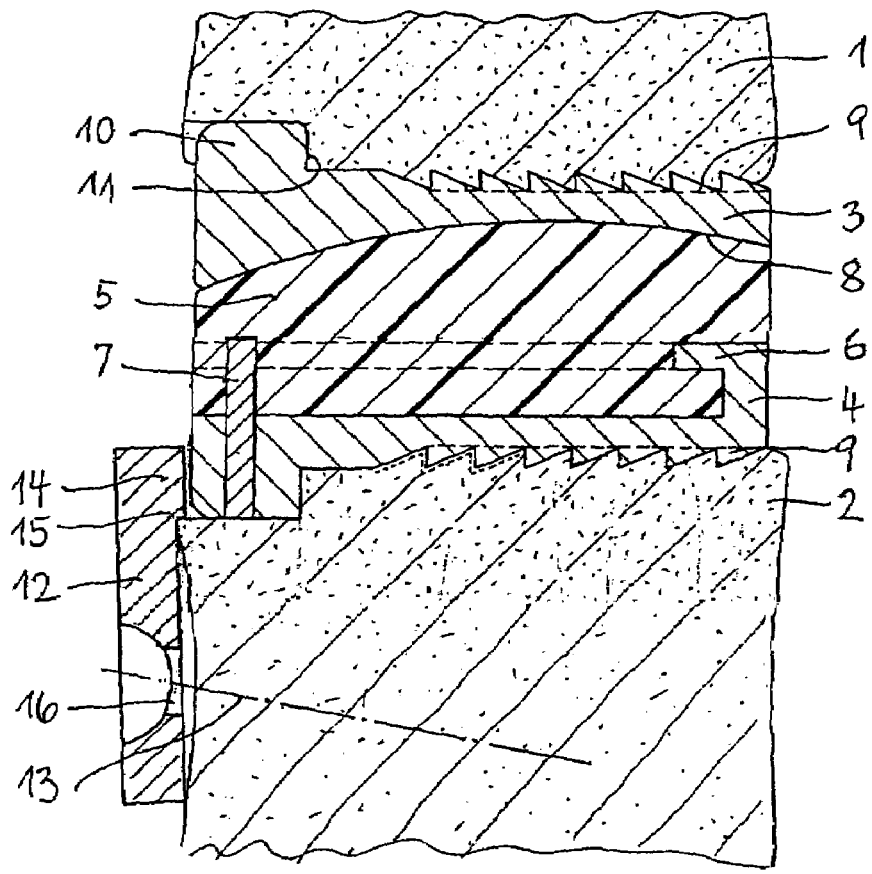
FIG. 1 shows a sagittal section through the prosthesis in the implanted state.

Between the vertebrae 1 and 2 of the cervical spine there is an intervertebral space into which is inserted the intervertebral prosthesis consisting of an upper cover plate 3, a lower cover plate 4, and a prosthesis core 5. The prosthesis core 5 is held on the lower cover plate 4 by profiles 6 and a catch 7. With the upper cover plate 3, it forms a slide surface pairing 8. The cover plates 3 and 4 have a sawtooth formation 9 by means of which they are held on the associated end plates of the vertebral bodies 1, 2. Short flanges 10 with dorsally facing limit stop surfaces 11 ensure that the cover plates 3, 4 cannot move farther than is wanted in the dorsal direction relative to the vertebral bodies 1, 2. An undesired movement in the ventral direction is generally prevented by the sawtooth formation of the profiles 9. This at least applies several months after the operation, when the bone tissue has grown into the surface of the cover plates and has connected firmly to them. Details of this construction are described in the publication WO 03/075804 A1.

There are cases where, because of special physiological circumstances, a risk of ventral displacement of the prosthesis must be taken into account. This risk may also arise for a period until the abovementioned connection between the cover plates and the bone tissue is secure. In these cases, the cover plate in question is combined with a securing plate 12 which, in the example in FIG. 1, is attached to the ventral surface of the caudal vertebral body 2 by means of screws 13. A part of the securing plate 12 designated as limit stop part 14 extends above the vertebral body 2 in such a way that it lies in front of part of the associated prosthesis cover plate 4. If the latter has a tendency to move out of the intervertebral space in the ventral direction, it will strike against the limit stop part 14 of the securing plate 12 and thus be prevented from moving any farther in this direction.

The securing plate 12 is shown on the caudal vertebral body 2. However, a securing plate could be attached, in addition or instead, to the cranial vertebral body 1.

The way in which the securing plate is attached is not important as regards the invention. The most obvious way is to use bone screws, expediently provided with a means (not shown) to secure them against loosening. They can be screwed in substantially parallel to the main plane of the prosthesis in the vertebral body. It is particularly advantageous for them to be inclined away from the prosthesis in the dorsal direction, as is depicted.

The securing plate 12 does not have to be positioned with great precision. It suffices if it is placed at a suitable location, preferably over a large part of the width of the prosthesis, and extends into the path which the prosthesis would take in the event of an undesired movement in the ventral direction. For this, it suffices if it extends 1 or 2 mm above the edge 15 of the vertebral body 2. It should not extend any more than about 2.5 to 3 mm above it, so as not to impede the relative flexion movement of the vertebral bodies 1, 2 and of the prosthesis parts.

To make the positioning easier, the securing plate 12 can be provided with an edge 15 which corresponds to the edge, designated by the same reference number, of the vertebral body 2 and separates the limit stop part 14 of the securing plate from that part which is to be fastened to the front surface of the vertebral body. When the limit stop part 14 has the desired height of about 2 mm, the surgeon proceeds by placing the securing plate on the vertebral body 2 in such a way that the edges 15 of the securing plate and vertebral body lie on one another. He then drills the holes for receiving the fastening screws 13 by using the screw holes 16 in the securing plate as drill gauges. In this way, he achieves a secure positioning.

Figure 3:
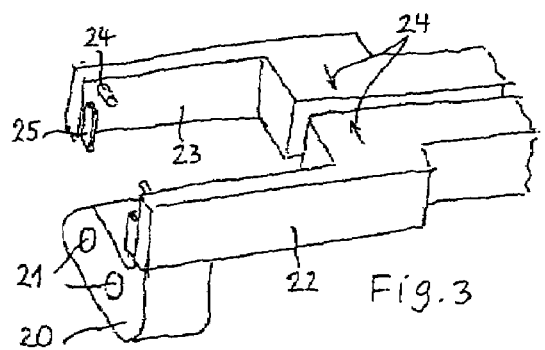
FIG. 3 shows a drill gauge for the fastening screws of the securing plate.
Figure 2:
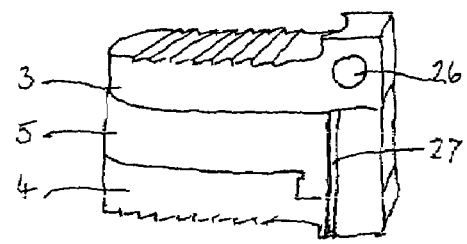
FIG. 2 shows a side view of the prosthesis without securing plate.

A still more secure positioning is achieved by using the instrument shown in FIG. 3. A drill gauge 20 with bore holes 21 for guiding the drill is arranged on a forceps-like instrument having two arms 22, 23 which, by means not shown, can be moved toward one another in the direction of arrow 24 and can be fixed in the approximated position. On their flanks facing one another, the arms 22, 23 have projections 24, 25 which are of a configuration that matches the corresponding recesses 26, 27 of the prosthesis, and, in the example shown, these projections are specifically pins 24, which correspond with bores 26, and blades 25 which correspond with slits 27. After the prosthesis 3, 4, 5 has been inserted into the intervertebral space, as is shown in FIG. 1, the instrument is applied to the prosthesis and adjusted thereon with the aid of the elements 24 to 27. The bores 21 of the drill gauge 20 are now located on the same axis in a position in which the bores are intended to be provided for the fastening screws 13 of the securing plate.

The instrument shown in FIG. 3 is especially suitable for a securing plate to be arranged in the caudal direction from the prosthesis. This is due to the arrangement of the elements 24 to 27. To prepare for a securing plate which is to be fastened in the cranial direction, it can also be equipped with a corresponding drill gauge on its top face as viewed in FIG. 3.

Seen from the ventral direction, the securing plate shown in FIG. 1 can be made slightly rectangular or oval with a greater dimension in the lateral direction than in the caudal-cranial direction. In a particularly advantageous embodiment, it is designed as a circular disk, like a clothes button, with a screw hole at its center. The advantage of this embodiment is that, during the operation, attention need be paid only to a correct positioning of the fastening screw, not to the orientation of the securing plate. The shape of the circular disk also has the advantage that it is less likely to cause irritation of the surrounding organs than is a rectangular plate. This applies especially if the edges, in particular the ventral edges, are rounded.

The securing plate can be made of metal or of a sufficiently resistant plastic. If the cover plate interacting with it is made of metal, a plastic is preferably chosen, or a plastic insert which forms the dorsally oriented surface of the limit stop part 14.

If the securing function of the securing plate is needed only temporarily, for example until the cover plates of the prosthesis have fused sufficiently with the adjoining bone tissue, the securing plate and its fastening means, for example the screw 13, can be made of biodegradable material. Such material is known and, therefore, does not have to be explained here. It is attacked and somehow broken down by the body. The time it takes for this to happen can be influenced by the choice of material. It is chosen such that the securing plate and its fastening means can exert a sufficient securing force for as long as is necessary, for example for a period of four months after the operation.

What is claimed is:

1. A cervical intervertebral prosthesis, comprising two cover plates configured to be connected to adjacent vertebral bodies, a securing plate separate from the cover plates which secures only one of the cover plates and is configured to be fastened to a ventral surface of one of the vertebral bodies and a prosthesis core which forms an articular joint with one of the cover plates, wherein at least one of the cover plates is provided with a limit stop surface facing in a dorsal direction relative to the vertebral bodies configured to lie against its associated adjacent vertebral body and formed by a rear side of a transverse flange on a ventral edge of the at least one of the cover plates relative to an implanted position.

2. The cervical intervertebral prosthesis according to claim 1, wherein the securing plate is biodegradable.

3. The cervical intervertebral prosthesis according to claim 2, wherein the securing plate is a circular disk.

4. The cervical intervertebral prosthesis according to claim 3, wherein the securing plate is a circular disk.

\* \* \* \* \*

UNITED STATES PATENT AND TRADEMARK OFFICE
CERTIFICATE OF CORRECTION

| | | |
|---|---|---|
| PATENT NO. | : 7,175,662 B2 | Page 1 of 1 |
| APPLICATION NO. | : 10/814783 | |
| DATED | : February 13, 2007 | |
| INVENTOR(S) | : Helmut D. Link et al. | |

It is certified that error appears in the above-identified patent and that said Letters Patent is hereby corrected as shown below:

In the Specification:

Column 1, lines 47 through 53, delete "However, it is unable to prevent the cover plate from shifting in the dorsal direction. The invention is therefore preferably intended for those cover plates which are equipped with suitable means for preventing this dorsal movement. Cover plates provided with a dorsally facing limit stop surface (WO-A-03 075 804) are therefore especially suitable."

In the Claims:

Column 4, line 45, insert the phrase --and not connected to-- between the words "from" and "the."

Signed and Sealed this

Eighth Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 7,175,662 B2 Page 1 of 1
APPLICATION NO. : 10/814783
DATED : February 13, 2007
INVENTOR(S) : Helmut D. Link et al.

It is certified that error appears in the above-identified patent and that said Letters Patent is hereby corrected as shown below:

In Claim 4, column 4, line 62, delete "3" and replace with --1--.

Signed and Sealed this

Seventh Day of October, 2008

JON W. DUDAS
*Director of the United States Patent and Trademark Office*